United States Patent [19]

Schoner

[11] Patent Number: 4,578,167

[45] Date of Patent: Mar. 25, 1986

[54] CELL FUSION
[75] Inventor: Wolfgang Schoner, Hanover, Fed. Rep. of Germany
[73] Assignee: Biofusion, Inc., Newton, Mass.
[21] Appl. No.: 426,114
[22] Filed: Sep. 28, 1982
[51] Int. Cl.[4] .................... G01N 27/26; G01N 27/28
[52] U.S. Cl. ............................ 204/183.1; 204/299 R
[58] Field of Search ........... 204/299 R, 180 R, 183.1; 435/172, 173, 287, 803

[56] References Cited

U.S. PATENT DOCUMENTS 4,326,934  4/1982  Pohl ........................... 204/180 R
4,441,972  4/1984  Pohl ........................... 204/180 R

OTHER PUBLICATIONS

Febs Letters, "Giant Culture Cells by Electric Field-Induced Fusion", Pilwat, Richter, and Zimmerman, vol. 133, No. 1, Oct. 12, 1981, pp. 169–174.
Naturwissenschaften, "Electric-Field-Stimulated Fusion: Increased Field Stability of Cells Induced by Pronase", Zimmermann and Pilwat, 68.Jahrgang, Heft 11, Nov. 1981, pp. 577–579.
Zeitschrift fur Naturforschung., "Membrane Fusion and Deformation of Red Blood Cells by Electric Fields", Scheurich and Zimmermann, vol. 35c, No. 11/12, Nov./Dec. 1980, pp. 1081–1085.
Febs Letters, "Electric Field-Induced Fusion: Electro-Hydraulic Procedure for Production of Heterokaryon Cells in High Yield", Vienken and Zimmermann, vol. 137, No. 1, Jan. 11, 1982, pp. 11–13.
Naturwissenschaften, "Giant Human Erythrocytes by Electric-Field-Induced Cell-to-Cell Fusion", Scheurich and Zimmermann, 68.Jahrgang, Heft 11, Jan. 1981, pp. 45–47.
Wesley, "Electric Field Cell Fusion Method Promises Rapid, Stable Production of Hybridomas", Genetic Engineering News, pp. 1 and 34 (Jul./Aug. 1982).
Unidentified one page paper referring to work done by Ulrich Zimmermann.
Zimmermann et al., "Fusion of Avena Sativa Mesophyll Cell Protoplasts by Electrical Breakdown", Biochimica et Biophysica Acta, vol. 641, pp. 160–165 (1981).
Teissie et al., "Electric Pulse-Induced Fusion of 3T3 Cells in Cells in Monolayer Culture", Science, vol. 216, pp. 537–538, (Apr. 30, 1982).
"Living Cells Generate, Respond to Electricity", Chemical & Engineering News, pp. 20–21 (Apr. 26, 1982).
Bloemendal, H. et al., Zone Electrophoresis in Blocks and Columns, Elsevier Publishing Co., New York, (1963), pp. 10–12.
The Condensed Chemical Dictionary, Van Nostrand Reinhold Co., New York, (1973), p. 902.
Halfmann, H. J., "Transfer of Mitochondrial Function into Cytoplasmic Respiratory-Deficient Mutant of Saccharanyces Yeast by Electro-fusion"Current Genetics, vol. 6, pp. 25–28, (Oct. 1982).
Zimmermann, U., et al., "Electric Field-Induced Cell-to-Cell Fusion", Journal of Membrane Biology, 67, 165–182, (May 1982).
Crane, J. S., Pohl, H. A., "A Study of Living and Dead Yeast Cells Using Dielectrophoresis", J. Electrochem. Soc., 6/68, pp. 584–586.
Pohl, H. A., Hawk, I., "Separation of Living and Dead Cells by Dielectrophoresis", Science, vol. 152, Apr. 29, 1966, pp. 647–649.
Pohl, H. A., "Theoretical Aspects of Dielectrophoretic Depositon and Separation of Particles", J. Electrochem. Soc., Jun. 1968, vol. 115, pp. 155C–161C.

Primary Examiner—Andrew H. Metz
Assistant Examiner—B. J. Boggs, Jr.

[57] ABSTRACT

Apparatus for fusing cells by applying an alternating voltage across a pair of spaced-apart elongated electrodes. The electrodes form between themselves an elongated fusion chamber for receiving a suspension of cells to be fused. The electrodes have a cross-sectional shape adapted to produce an inhomogenous electric field within the fusion chamber suitable for inducing dielectrophoretic movement of suspended cells towards the electrodes and for maintaining strings or lines of two or more cells in contact with the electrodes along an elongated, narrow attachment zone on each electrode. A voltage pulse is applied across the electrodes after the cells have become attached thereto. The duration and amplitude of the pulse is selected to be sufficient to cause the strings of cells to fuse into a single cell. The depth of the fusion chamber below the level of the attachment zones is less than 2 mils, which is shallow enough to inhibit collection of cells below the attachment zones, thereby improving fusion efficiency.

7 Claims, 12 Drawing Figures

CELL FUSION

BACKGROUND OF THE INVENTION

The invention relates to cell fusion. It is often desirable in biochemical processes to fuse cells and thereby combine in one cell certain of the properties of the individual cells. Cell fusion is of particular interest in the production of monoclonal antibodies. Such antibodies are produced from a colony of identical cells all derived from a common ancestral cell. In order that the common ancestor be capable of reproducing itself, i.e., be immortal, it is formed by fusing a lymphocyte (e.g., a B cell from the spleen) that secretes the desired antibody with an immortal cancer cell such as myeloma cell.

Cell fusions are conventionally performed by suspending the cells in polyethylene glycol or another material capable of weakening or dissolving the cell membranes. This tends to cause a tiny fraction of the suspended cells to fuse, and the fused cells can then be separated.

Efforts have also been made to fuse cells by the action of an electric field. Zimmermann has reported successful fusions of plant protoplasts using the technique of subjecting the cells, first, to an alternating potential to collect them on the surfaces of two spaced apart electrodes (by the process known as electrophoresis) and, second, to a pulse designed to breakdown the cell membranes at the regions of contact between collected cells. Zimmermann et al., "Fusion of Avena Sativa Mesophyll Cell Protoplasts by Electrical Breakdown", 641 Biochimica et Biophysica Acta 160–165 (1981).

SUMMARY OF THE INVENTION

I have discovered techniques for successfully fusing human and other mammalian cells by action of an electric field. My discoveries make it possible to efficiently fuse human cells for the production of monoclonal antibodies.

In a first aspect the invention features reducing the volume of the fusion chamber between the electrodes so as to improve efficiency. In preferred embodiments, the volume is less than 20 microliters, and the transverse sectional area of the chamber between the electrodes is less than $10^{-4}$ in$_2$.

In a second aspect the invention features keeping the depth of the fusion chamber below the level of cell attachment shallow enough to inhibit collection of cells below that level. This improves fusion efficiency because cells collecting below the attachment zones tend not to participate in the fusion process. In preferred embodiments, the depth below the attachment level is less than 2 mils but greater than 1 mil.

In a third aspect the invention features electrode diameters of less than 20 mils. This helps increase the strength of the electric field at the vicinity of cell attachment, and it facilitates reductions in chamber volume. In preferred embodiments, the electrodes are cylindrical, and have diameters in the range from 3 to 12 mils.

In a fourth aspect the invention features sealing the fusion chamber so as to prevent evaporation and ensuing change of osmolarity during the fusion process. In preferred embodiments, the electrodes are separate from and inside of the walls of the chamber; the chamber walls are glass; the chamber comprises either an oval cross section capillary (in which holes have been formed for receiving the electrodes) or an assembly of bonded flat pieces of glass providing a rectangular internal cross section for better microscope viewing; the electrodes are heat welded or glued to the capillary interior; liquid insertion and liquid removal means (e.g., microsyringes) are attached at the ends of the capillary; the liquid insertion means supply cell suspension, cell-harvesting medium, and an osmolarity-controlling solution; and the liquid removal means includes an outlet tube for suspensions of fused cells and additional tubes adapted to inject liquid into the outlet tube in an outgoing direction at the point of the outlet tube's exit from the fusion chamber.

In a fifth aspect the invention features making the alternating voltage which creates the cell collecting field a sinusoidal voltage of a frequency sufficiently close to 2.0 megaHertz so as to cause cells to move toward and collect at said electrodes without the cells being harmed from electrolysis, loss of electrolyte, excessive spinning, or boiling. In preferred embodiments, the frequency is in the range from 1.9 to 2.1 megaHertz.

In a sixth aspect the invention features a fusion pulse with a duration of less than 20 microseconds. In preferred embodiments, the duration is equal to or greater than 1 microsecond; the pulse amplitude is sufficient to produce fusion in a single pulse; the pulse is applied within from 1 to 4 microseconds after cessation of the alternating voltage forming the collecting field; the alternating voltage is restored within 100 microseconds after cessation of the pulse; and the pulse amplitude is within the range from 5 to 150 V DC.

In a seventh aspect the invention features suspending the cells to be fused in an electrolyte free solution, thereby reducing heating of the suspension under the influence of the electrical field. In preferred embodiments, an electrolyte-free buffer solution (e.g., comprising histidine or trishydroxy-methylaminomethane) is added to the electrolyte-free suspension to keep the pH of the suspension in a neutral range (e.g., 7.2) suitable for maintaining human cells.

In an eighth aspect the invention features maintaining the osmolarity of the solution suspending the cells to be fused above 278 milliosmol/liter. In preferred embodiments, the osmolarity is kept with the range of 285–300 milliosmol/liter, most preferrably between 295 and 300 milliosmol/liter, and the osmolarity is adjusted during the fusion process to keep it within that range.

In a ninth aspect the invention features maintaining the cell concentration in the suspension of cells to be fused within the range of $10^5$ to $10^6$ cells/cc.

In a tenth aspect the invention features applying a protease selected to remove fusion-inhibiting proteins from the cell walls prior to application of the electrical field. In preferred embodiments the protease is pronase, and the protease is added immediately before application of the field so as to reduce harmful effects of the protease.

Other features and advantages of the invention will be apparent from the following description of the preferred embodiment, and from the claims.

DESCRIPTION OF THE PREFERRED EMBODIMENTS

Preferred embodiments of the invention will now be described.

DRAWINGS

Figure 1:
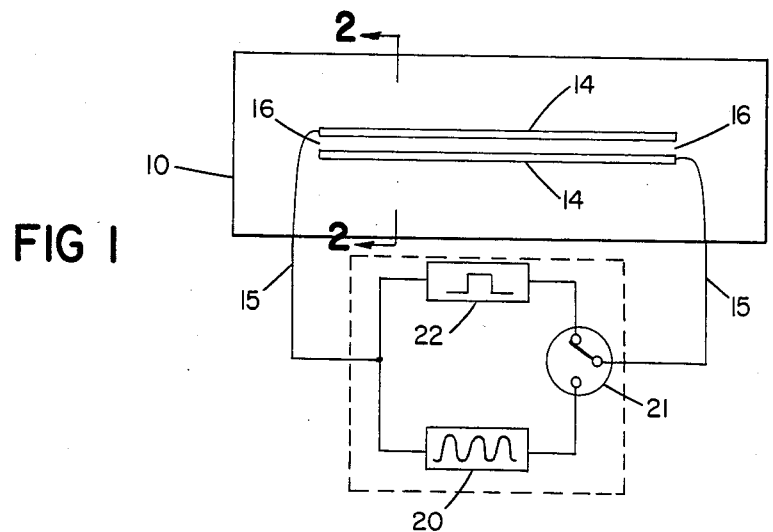
FIG. 1 is a plan view of one preferred embodiment including associated electronics shown in block diagram form.
Figure 2:
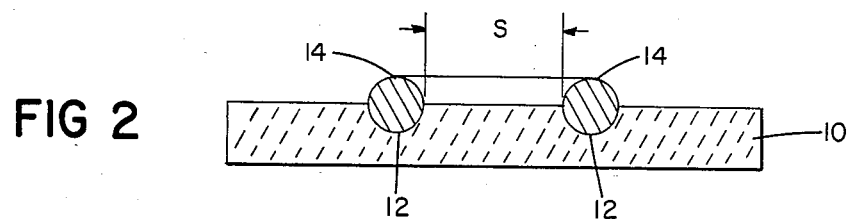
FIG. 2 is an enlarged cross sectional view taken along 2—2 of FIG. 1.
Figure 3:
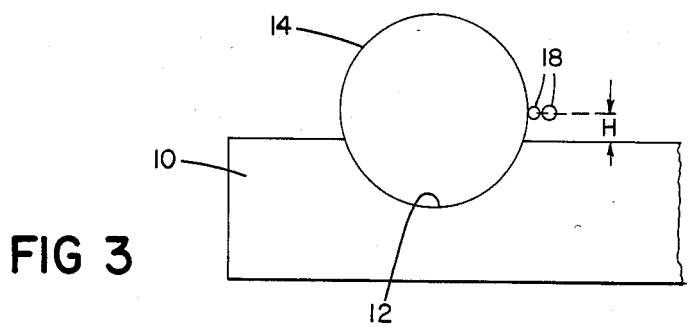
FIG. 3 is an enlarged view of a portion of FIG. 2, showing diagrammatically the orientation of two cells as they would typically appear at one step in the fusion method of the invention.

Referring to FIGS. 1-3, there is shown one embodiment of my cell-fusion device. Glass slide 10 has parallel grooves 12 each receiving a cylindrical wire 14 (pure platinum preferred; platinum-iridium and stainless steel are alternatives), 8 mils in diameter. Wires 14 are spaced apart (dimension S) by 7 mils and are retained on the glass slide by epoxy 16 applied at each longitudinal end (a thin layer (not shown) of epoxy wicks along the entire length of the capillary formed by the two wires). To assure snug contact of wires 14 within grooves 12, all along each wire's length, each wire's natural shape, prior to insertion into the grooves, is slightly curved upward at each end, so that upon epoxying the ends there remains a slight downward pressure of the wire on the glass. Grooves 12 each have a depth equal to one-half the wire diameter reduce by dimension H (FIG. 3), which is 1-2 mils. During fusion, the influence of the electric field generated between wires 14 tends to cause cells 18 to line up all along both wires at midway line L (the line of contact of a vertical tangent plane with the cylindrical wire). Dimension H (which is the height of the midway line above the surface spanning between the wires) is chosen small enough to inhibit collection of cells in the zone below the midway line where they would not be fused.

Figure 4:
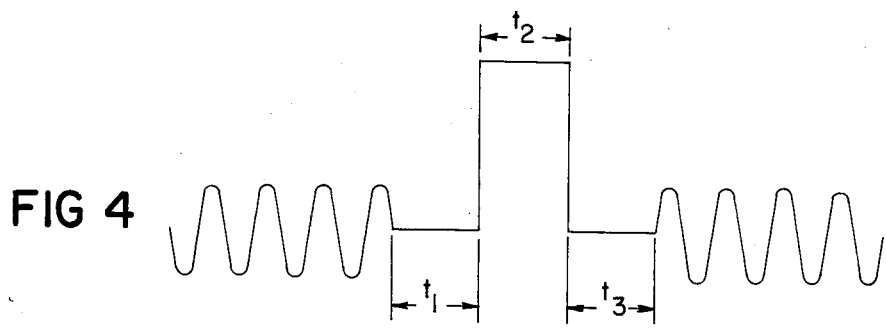
FIG. 4 illustrates the voltage-time histogram of the cell-collecting field and the fusion-causing impulse.

Each wire 14 is connected by a lead 15 to one side of electrical function generators 20, 22, connected in parallel. Generator 20 supplies a 1.9-2.1 megaHertz (most preferably 2.0 megaHertz) pure sine wave of 0-30 volts peak-to-peak amplitude. Generator 22 supplies a single square-shaped pulse of 1 to 20 microseconds duration and of sufficient amplitude to cause cell fusion (from 5 to 150 volts DC). The rise time of the pulse is made rapid enough so that the pulse sees very little impedance from the capacitance of the cells. Switch 21 switches between the sine-wave and pulse inputs. Delay $t_1$ (FIG. 4) of switch 21, the delay between cessation of the sine wave and rise of the square-shaped pulse, should preferably be less than 5 microseconds and most preferably in the range of 1 to 5 microseconds. Delay $t_3$, between cessation of the pulse and renewed onset of the sine wave, should preferably be less than 100 microseconds, and most preferably less than 20 microseconds.

Figure 5:
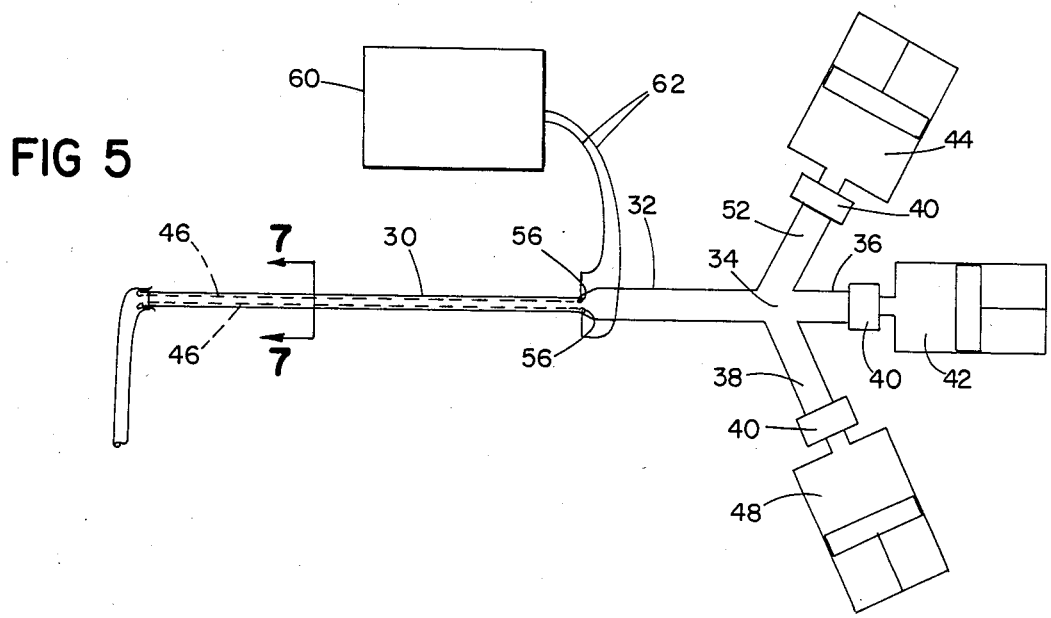
FIG. 5 is a plan view, partially cut away, showing a second preferred embodiment.
Figure 6:
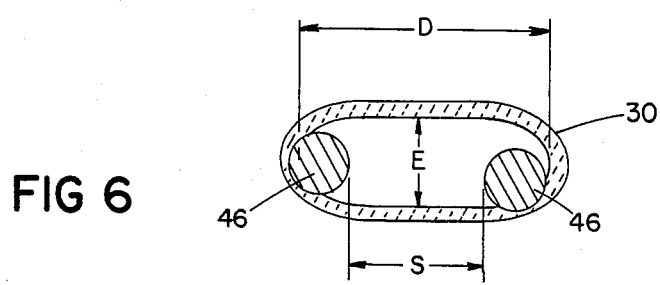
FIG. 6 is a cross sectional view taken along 6—6 in FIG. 5.
Figure 7:
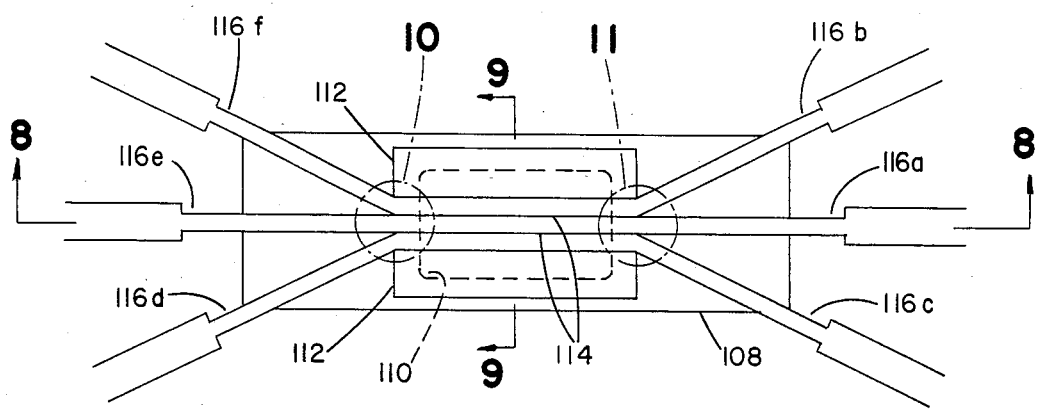
FIG. 7 is a plan view of a third preferred embodiment, which is presently most preferred.

Referring to FIGS. 5-6, there is shown a second embodiment of my cell fusion device. Glass capillary 30 extends from glass tubing 32, which is separated at 34 into three branches 36, 38, 52, which are, in turn, connected via Luer-lock fittings 40 to syringes 42, 44, 48, which are filled with cell suspension, cell harvesting medium, and cell-free buffered-mannitol solution (for adjusting osmolarity), respectively. Capillary 30, shown in cross section in FIG. 6, receives wires 46 (4 mil diameter platinum) through small holes 56 at its ends. Commercially-available X60 glue is used to secure wires 46 at each of holes 56 and to seal the opening between each wire and hole. The capillary is a commercially-available oval cross-section capillary with internal dimensions D of about 12 mils and E of about 4 mils. Wire gap S is about 4 mils. Function generators 20, 22 are contained in control device 60, connected to wires 46 by leads 62.

Wires 46 are embedded in the interior wall of the capillary by (1) pre-curving them slightly, (2) inserting them through holes 56 at each end, and (3) applying a small electrical current sufficient to heat the wires to a temperature above the melting point of glass but below that of the wire. Some asymmetry of the wires with respect to the capillary ordinarily results (as shown in FIG. 6), because of the difficulty of working with such fine wires and capillary, but this does not substantially affect the fusion process.

With this second embodiment, a 6.4 V, 2 MHz collecting voltage and a 28 V fusion pulse 20 microseconds long has been successfully used in fusing human B cells.

Figure 8:
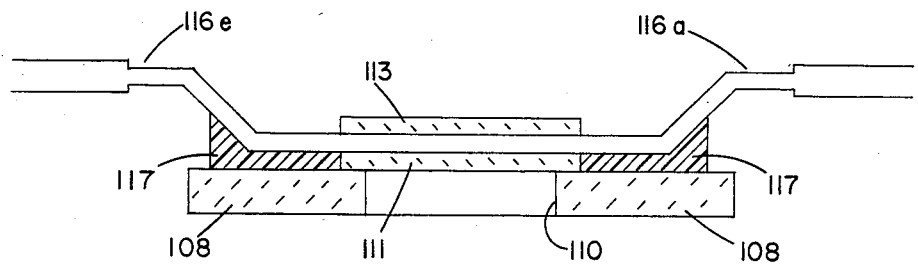
FIG. 8 is a cross section taken along 8—8 in FIG. 7.
Figure 9:
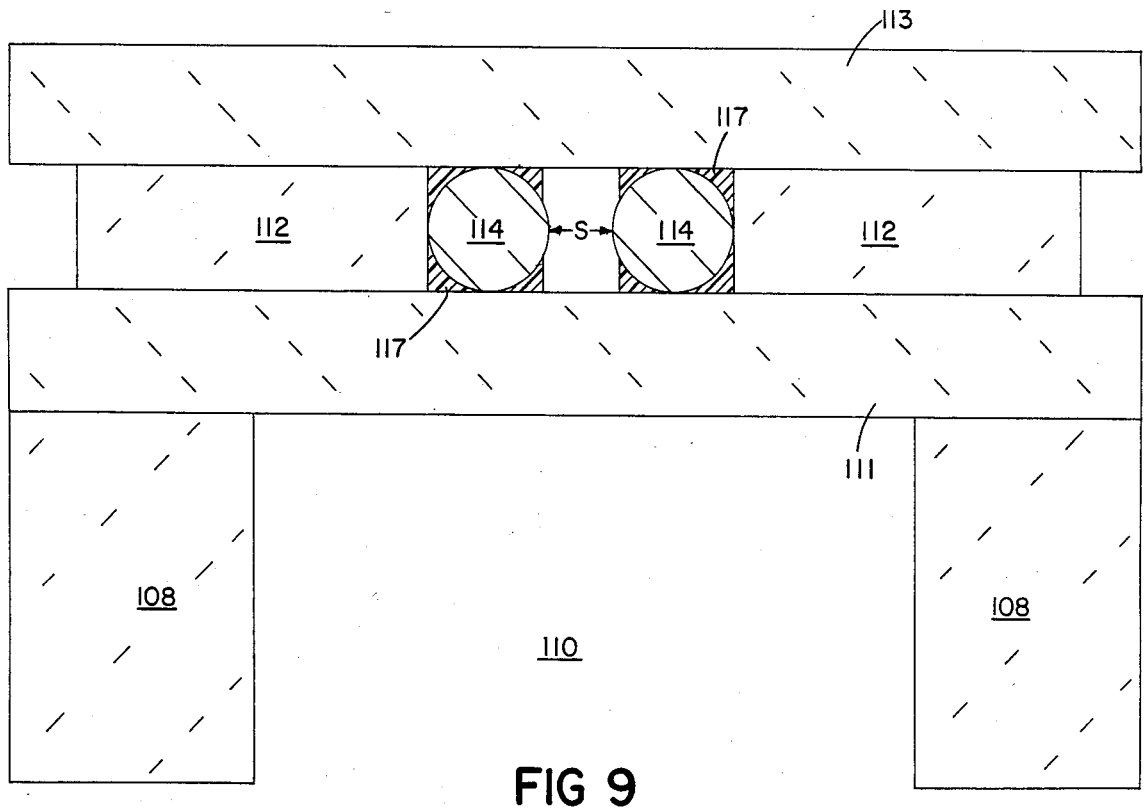
FIG. 9 is an enlarged cross section taken along 9—9 in FIG. 7.
Figure 11:
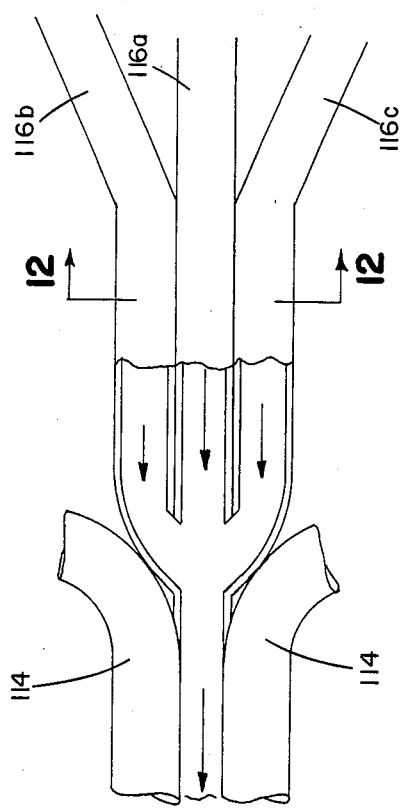
FIG. 11 is an enlarged, highly diagrammatic, view of region 11 in FIG. 7.
Figure 10:
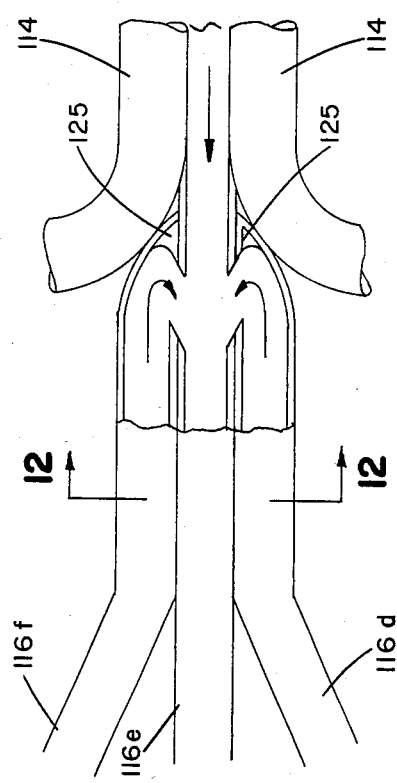
FIG. 10 is an enlarged, highly diagrammatic, view of region 10 in FIG. 7.
Figure 12:
FIG. 12 is a cross sectional view at 12—12 in FIGS. 10 and 11.

There is shown in FIGS. 7-12, a third, and presently most preferred, embodiment for practicing the invention. Standard glass slide 108, with cut out region 110 (1 cm × 1.3 cm), has glued to its top surface over the cut out region three thinner glass slides 111, 112, 113 (each 101.6 microns thick and 1.5 cm long). The middle slide 112 is longitudinally split into two pieces, to form a narrow chamber 12 mils wide, 4 mils deep, and 1.5 cm long. Two platinum wires 114 (each 4 mils in diameter) are glued with nonconductive epoxy to the side of the chamber as shown in FIG. 9. (Epoxy could also fill the bottom of the region between the wires to reduce the chamber volume below the level of cell attachment so as to inhibit collection of cells in that bottom region.) The separation S between the wires is 4 mils. To fill the chamber with cell suspension and flush it after fusion, three glass capillaries 116a, 116b, 116c, 116d, 116e, 116f (each with a 100 microns outside diameter) are attached (by epoxy glue) at each end. As shown in FIGS. 10 and 11, the glass capillaries are glued in parallel formation at the region of connection to the chamber ends; the glue 117 also supports the capillaries from beneath, as shown in FIG. 8.

As indicated in FIGS. 10 and 11 by the flow direction arrows, five of the capillaries serve as fluid inlets, and only one, capillary 116e carrying departing fused cells, serves as an outlet. Capillary 116c carries the incoming cell suspension. Protease is injected through capillary 116b. A buffered mannitol solution for adjusting osmolarity is supplied through capillary 116c. Capillaries 116d, 116f, which straddle cell outlet capillary 116e, are used to add fluids (such as $CaCl_2$ solution and nutrients) to the fused cell suspension that has left the chamber. Holes 124 and baffle-like portions 125 at the ends of capillaries 116 cause fluid injected through capillaries 116d, 116f to reverse direction and depart through capillary 116e. This arrangement allows liquid to be added to the departing fused-cell suspension as it flows out of the fusion chamber, and it also permits outlet capillary 116d to be flushed without having to pass the flushing liquid through the fusion chamber. Wires 114 enter the chamber on either side of the three capillaries, and the ends of the chamber are sealed with epoxy. Microsyringes (manufactured by Hamilton, Reno, Nev.) or automatic micropumps are attached to the capillaries via tubing (neither of which is shown).

The general procedure for achieving cell fusion is as follows:

(1) A special, electrolyte-free 1.0 molar buffer solution of tris-hydroxy-methylaminomethane ("tris") is prepared by dissolving crystals of tris-hydroxymethylaminomethane in distilled sterilized water. (Ordinary medical tris buffer-solution contains electrolyte impurities and is thus unsuitable, because such a solution would heat up intolerably under influence of the applied electrical fields.)

(2) An electrolyte-free mannitol solution of proper physiological osmolarity is prepared, and its pH is adjusted to 7.2 by drop-wise addition of the special buffer. The buffer corrects for the natural pH shift occurring in the mannitol solution owing to exposure to $CO_2$ in the ambient. An alternative to the tris buffer is Histidin (an amino acid), which is electrolyte free and can be added to correct the pH of the sugar solution.

(3) Mammalian cells to be fused are washed and suspended in the buffered mannitol solution, and the solution is supplied to the fusion chamber. On the order of 2,000 cells (before fusion) are applied at a time. Before application of the cell suspension a protease solution is added in order to remove fusion-inhibiting surface proteins from the cell membranes.

(4) Function generator 20 is turned on for 5-50 seconds, to apply the 2 MHz alternating potential for long enough to line cells up as shown in FIG. 3. The amplitude of the alternating potential is adjusted so as to form an inhomogenous electrical field of 600-800 V/cm average strength, with field strength increasing from a low midway between the wires to a maximum at lines L on the wire surfaces (the lines of intersection of tangent vertical planes and the cylindrical wires). The alternating field causes the mammalian cells to dielectrophoretically orient themselves in the field, much like true dipoles. The dielectrophoretically-oriented cells drift toward one or the other wire because of the gradient in the electrical field. After a short time (less than 50 seconds) some cells make contact with the wires along lines L, where the electrical field is strongest. Additional cells arriving at the vicinity of the wire tend largely to stack up behind, and in contact with, cells already adhered to the wire, so that strings or chains of cells are formed. Most typically such strings are two cells long, but depending on the alternating potential applied the strings can be as long as ten or more cells. A light microscope is used to observe the process. It is the difference in size of the cells being fused that accounts for the fact that cells tend to line up in the right combinations, i.e., that, when fusing cells X to cells Y, one gets XY combinations at the wires rather than XX or YY. Larger cells tend to attach first to the wire, so that in the suspension of normal and transformed B-cells described in the protocol below the larger transformed B-cells are first to adhere and are followed by the smaller normal B-cells, which tend to adhere not to the wire but to the larger transformed B-cells already adhered thereto. The number (two or more) of cells in any line of cells is dependent in part on the amount of time that the collecting field is left on. By observing the collection process through the microscope, it is possible to initiate fusion at a time when the desired number and combination of cells are lined up. It is generally necessary only to view at one location as there is good uniformity of cell behavior all along both wires.

(5) After the lining up of cells is complete, function generator 22 is used to apply a single 1-20 microsecond ($t_2$) pulse (FIG. 5). A one to five microsecond delay ($t_1$) is allowed between cessation of the alternating potential and onset of the pulse in order that cells remain adhered as shown in FIG. 4a during the fusion pulse. The pulse causes the cell membranes to break down sufficiently for the cell in each line then to begin to fuse. Complete fusion is generally complete in from 10 seconds to a maximum of 20 minutes. After the pulse ends, the alternating potential is restored, within less than 100 microseconds, or more preferably within less than 20 microseconds ($t_3$), to keep the cells adhered to the wires. A longer delay is permissable but results in the fused cells drifting away from the wires and out of the microscope field of view.

The amplitude of the fusion pulse typically varies with different cells and is chosen experimentally by repeating the pulse, each time with a slightly greater amplitude, while observing cell behavior through a microscope. When the pulse voltage is too low a pair of cells at the wire (such as shown in FIG. 4a) tend to drift apart during the interval ($t_1+t_2+t_3$) in which the alternating potential is turned off. Too high a voltage, on the other hand, results in bursting of the cells.

Sweeping of the cells toward the wires in strongly a function of the average field strength and, thus, of the applied potential and separation S of the wires. The preferred range on the separation S is less than 7 mils and most preferrably in the range 3 to 7 mils; the embodiments described have 4 and 7 mils.

The tendency of the cells to remain adhered to the wire and each other is, on the other hand, strongly a function of the wire diameter, as the smaller the wire diameter, the greater the local field strength in the vicinity of the wire's surface. Wire diameters ranging from 3-12 mils (75-300 microns) are preferable, although some cell adherence and fusion has been obtained with a diameter as great as 20 mils (500 microns).

Wire diameter, wire separation, and applied voltage must also be kept within ranges which do not result in so much power being passed through the liquid as to heat it above ambient temperature, and thus kill the cells. Cooling could, if necessary, be achieved, however, by flushing liquid continuously over the sealed fusion chambers of FIGS. 5 and 7.

The advantage of the sealed fusion chambers of the second and third embodiments (FIGS. 6-13) is that they prevent evaporation and change of osmolarity. A disadvantage, however, of the second embodiment is that the curvature of the capillary distorts microscope viewing. This problem is overcome in the third embodiment.

An important feature of the fusion chamber is its small size, which has the advantage of greatly increased fusion efficiency. With a small chamber volume, a greater fraction of cells tend to attach to the electrodes and be fused because there is less wasted volume away from the attachment zones and thus less volume in which cells can collect. Furthermore, it is possible to work with very small numbers of cells, a common situation when some of the cells being fused are rare. In the elongated chambers shown in the embodiments, the transverse sectional area between the wires is a good indicator of chamber size, because chamber length is less important to fusion efficiency. In the third embodiment, the transverse sectional area between the wires is approximately $0.16 \times 10^{-4}$ in$^2$ (4 mil $\times$ 4 mil). The overall volume between the wires in that embodiment is about 0.20 microliters. I prefer that chamber volume be less than 20 microliters and that the transverse sectional area between the wires be less than $1.0 \times 10^{-4}$ in$^2$ (which corresponds roughly to a 12 mil wire and an 8 mil gap between the wires).

Cell concentration in the solution is also important; the preferred range is $10^5$–$10^6$ cells/cc. If the concentration is too high, the lines of cells adhered to the wire tend to be so close that fusion can occur between cells in adjacent lines as well as between cells in the same line. The latter is more desirable in order that the procedure give repeatable results.

The optimum cell collecting field strength varies somewhat with the type of cell being fused. Too low an amplitude results in the cells not lining up at the electrodes. Symptoms of too high an amplitude are (1) cells that melt together and die, (2) cell chains that bend away from straight, and (3) elongated rather than round cells.

For reasons not entirely understood, it is important that the alternating field be nearly a pure 2.0 MHz sine wave; a shift in frequency below 1.9 or 2.1 MHz has been observed to be less effective at lining up the cells, sometimes causing the cells to merely rotate. If the frequency is outside the 1.9-2.1 MHz range, either higher or lower, the cells also tend to die from any one of the following: electrolysis (release of H$_2$ at the wires), loss of electrolyte, excessive spinning, or boiling.

Proper physiological osmolarity and pH must be constantly maintained throughout the fusion process. If the solution is overheated, the osmolarity can leave the most preferred 295–300 milliosmol/liter range. At a minimum the osmolarity should be greater than 278 milliosmol/liter, and preferably above 285 milliosmol/liter. The advantage of staying within the most preferred 295–300 range is that the cells do not swell and thus their membranes do not tighten. This leads to improved fusion efficiency because the untightened cell membranes tend to respond better to the fusion pulse.

The 1–20 microsecond duration of the fusion pulse is determined by the fact that too long a pulse (i.e., longer than 20 microseconds) makes the amplitude setting (which must be determined by experiment for each type of fusion) too sensitive, i.e., there is too little spread between the amplitude that will induce fusion and the amplitude that will cause cell bursting, thus resulting in a greatly reduced survival rate for fused cells. The low end of the range, 1 microseconds, was determined by observing that below that figure fusion generally could not be achieved at any amplitude without damaging the cells.

Osmolarity of the cell-containing solution must be carefully measured. It is generally not sufficient to simply prepare a large-volume solution of the desired concentration. Rather, it is necessary to check the actual sample of solution being used with an osmolarity meter, and then add concentrated mannitol or distilled water as needed.

After fusion is complete, the glass slide or capillary is flushed with cell-harvesting medium (indicator free), and conventional procedures are followed to separate the fused cells from the solution. Using the second and third embodiments permits performing serial fusions by the following procedure: (1) fill the capillary with a cell suspension; (2) perform fusion procedure; (3) flush with cell-harvesting medium; (4) flush with cell-free, sugar solution; and (5) repeat the procedure, beginning with step 1.

Fusion of normal human B-cells and non-secreting, transformed (malignant) B-cells has been accomplished with the third embodiment using the following procedure:

1. Each group of cells was separately washed:
    (a) Each was suspended in Hanks Balanced Salt Solution (HBSS), and spun at 4° C. for 10 minutes at 1200 RPM (600 G).
    (b) The solution was removed by suction.
    (c) The cells were resuspended in a specially-prepared 295 milliosmol/l mannitol-tris solution (pH 7.2) at room temperature and then spun at 4° C. (600 G) for 10 minutes at 1100 RPM. The mannitol-tris solution used was prepared by adding 10.2 g of mannitol to 200 ml of distilled water, mixing 2 microliters of that mannitol solution with 18 microliters of a specially-prepared tris solution (36.4 g of pure tris-hydroxymethylaminomethane (THAM) crystals per 100 ml of distilled water) then adding enough of the 20 microliters of mannitol-tris solution to the original 200 ml mannitol solution to bring the pH to 7.18, and finally adjusting the osmolarity of the solution to 295 milliosmol/l.
    (d) Steps (b) and (c) were repeated twice, each time spinning at 22° C. for 10 minutes, so as to wash the cells three times in the mannitol-tris solution.
2. The two types of B cells were then counted.
3. The two cell suspensions were then mixed to achieve a 1:9 ratio of transforemd to normal B-cells in a 100 microliter sample for a total cell concentration of $10^5$ to $10^6$ cells/ml, and the fusion chamber was filled (through capillary 116a) with 0.18 microliters of the mixed-celled suspension. The large ratio of transformed cells to normal cells was used to reduce the chance of fusion between two transformed cells and the resulting secretion of harmful proteins therefrom. (This ratio may, however, be undesirable in the typical situation wherein the normal B cells are available only in small numbers and at large cost.)
4. Simultaneously, 0.02 microliters (1/9 of the cell suspension volume) of a pronase solution (100 mg/100 ml at 2° C.), a particular protease selected for its ability to remove fusion-inhibiting proteins from the cell walls, was added to the fusion chamber through capillary 116b.
5. The chamber was placed in a light microscope.
6. A collecting field was applied to 25 seconds using a 2 MHz, 0.5–20 V alternating potential voltage, to create a 0.9 V/cm average field. Following that, a fusion pulse 1–20 microseconds long was applied. Then the collecting field was restored.
7. After 3 minutes, long enough for fusion to be largely completed, the collecting field was turned off, and the chamber was flushed with 37° C. mannitol-tris (or Histidin) into a microtiter plate or equivalent container having many small recesses in which cells can be grown. After fusion, the cell membranes are weak and active cell chemistry is necessary for survival.

The warm 37° C. solution is used to achieve this desired speeding up of cell chemistry.

8. After 20 minutes the temperature is brought down with a NaCl$_2$ solution (0.9%) including 1 mMol CaCl$_2$ added via capillary 116d. The CaCl$_2$ helps reseal the cell membranes. The CaCl$_2$ is added late enough so that Ca ions do not penetrate the membrane in sufficient numbers to kill the cell.

9. After another 10–15 minutes the fused cells are washed in a solution of DMEM and fetal calf serum (without a phenolthaline indicator because the indicator could pass through the weak membranes).

10. After four days, separation of cells was performed using an Ortho III cell separator, and then the cells were grown in a feeder layer.

Fusion efficiency (number of XY fusions compared to total possible XY fusions, i.e., the number of transformed B cells in this example) was approximately 70%.

Hybridoma identification was done by the conventional techniques described in Scan J. Immunol. 11, 437–444 (1980) and Somatic Cell Genetics, Vol. 7, No. 3, pp. 321–329 (1981).

In addition to fusion of human cells, the invention has been successfully applied to fusion of mouse and rabbit cells and human/mouse and human/rabbit fusions. Monoclonal antibodies have been successfully produced by fused human cell lines. To date fused human cell lines have remained alive for over one-half year.

Other embodiments of the invention are within the following claims.

What is claimed is:

1. The method of fusing cells, comprising the steps of suspending the cells in a solution between two elongated electrodes providing an inhomogenous alternating electrical field,
   allowing the cells to drift dielectrophoretically toward the electrodes and become attached thereto in strings or lines of two or more cells, and
   applying a voltage pulse across the electrodes to cause strings of cells to fuse into single cells,
   wherein the osmolarity of the actual sample of solution in which cells are to be suspended is measured and kept above 278 milliosmol/liter.

2. The method of claim 1 wherein said osmolarity is kept within the range of 285–300 milliosmol/liter.

3. The method of claim 2 wherein said osmolarity is kept between 295 and 300 milliosmol/liter.

4. The method of claim 1 wherein the osmolarity of said solution is kept within said range during the fusion process.

5. Apparatus for fusing cells, comprising
   a pair of spaced-apart, elongated electrodes,
      said electrodes forming between themselves an elongated fusion chamber for receiving a suspension of cells to be fused,
   first electrical means for applying an alternating voltage across said electrodes,
      said electrodes having a cross-sectional shape adapted to produce an inhomogenous electric field within said fusion chamber suitable for inducing dielectrophoretic movement of suspended cells towards the electrodes and for maintaining strings or lines of two or more cells in contact with said electrodes along an elongated, narrow attachment zone on each electrode,
   second electrical means for applying a voltage pulse across said electrodes after said cells have become attached thereto, the duration and amplitude of said pulse being sufficient to cause said strings of cells to fuse into a single cell, wherein the depth of said fusion chamber below the level of said attachment zones is less than 2 mils whereby it is shallow enough to inhibit collection of cells below said attachment zones, thereby improving fusion efficiency.

6. The apparatus of claim 5 wherein said depth is greater than 1 mil.

7. The apparatus of claim 5 wherein said apparatus further comprises a base to which said electrodes are attached along their length, said base forming the bottom surface of said fusion chamber and said base having grooves receiving said electrodes so as to raise the level of said bottom surface with respect to said attachment zones on said electrodes.

* * * * *